United States Patent [19]
Hasson

[11] Patent Number: 5,250,056
[45] Date of Patent: Oct. 5, 1993

[54] FORCEPS-TYPE SURGICAL INSTRUMENT

[76] Inventor: Harrith M. Hasson, 2043 N. Sedgwick, Chicago, Ill. 60614

[21] Appl. No.: 879,604

[22] Filed: May 7, 1992

Related U.S. Application Data

[63] Continuation-in-part of Ser. No. 830,681, Feb. 4, 1992.

[51] Int. Cl.$^5$ .............................................. A61B 17/00
[52] U.S. Cl. .................................. 606/151; 606/206; 606/207; 606/208
[58] Field of Search .................. 606/1, 126, 147, 148, 606/151, 205–208

[56] References Cited

U.S. PATENT DOCUMENTS

| 1,659,112 | 2/1928 | Littlejohn . | |
| 3,277,895 | 10/1966 | Johnson | 606/151 |
| 4,803,983 | 2/1989 | Siegel | 606/151 |
| 5,009,661 | 4/1991 | Michelson | 606/205 |
| 5,133,724 | 7/1992 | Wilson, Jr. et al. | 606/151 |

FOREIGN PATENT DOCUMENTS 0065054 11/1982 European Pat. Off. ............ 606/205

Primary Examiner—Stephen C. Pellegrino
Assistant Examiner—Jeffrey A. Schmidt
Attorney, Agent, or Firm—Wood, Phillips, VanSanten, Hoffman & Ertel

[57] ABSTRACT

A surgical instrument having first and second cooperating jaws that are movable relative to each other selectively between open and closed positions, structure for normally urging the jaws from their open position towards their closed position with a first predetermined force, there further being structure for urging the jaws towards the closed position therefor with a second predetermined force that is greater than the first predetermined force.

24 Claims, 5 Drawing Sheets

FORCEPS-TYPE SURGICAL INSTRUMENT

CROSS-REFERENCE

This application is a continuation-in-part of my co-pending application Ser. No. 830,681, filed Feb. 4, 1992, entitled "Surgical Instrument for Holding a Needle".

BACKGROUND OF THE INVENTION

1. Field of the Invention

The present invention relates to surgical or medical instruments of the forceps-type conventionally used for clamping and manipulating body tissues or organs and, more particularly, to a mechanism for selectively applying different locking forces on the jaws of such an instrument.

2. Background Art

Conventional forceps-type instruments normally include a pair of pivoted forceps jaws which function in a scissors-like action and are used in medical operations or surgery to hold, expose and manipulate tissues. The jaws may be self-biased to an open condition at the distal end of the instrument to define a V-shaped receptacle. A pair of graspable and relatively movable handles at the proximal end of the instrument are squeezed together to close the open distal jaw ends so as to grasp tissues, needles or the like between the jaws.

With the conventional forceps-type clamping instruments described above, activation of the jaws is accomplished by scissors-type action between the handles, requiring cumbersome manual manipulation by a surgeon and, over a prolonged use, may cause fatigue and tremors due to the necessary unnatural movements of the intrinsic hand muscles. Once the jaws are moved to a pressure-applying position, the unwieldy handle arrangement restricts the precision and finesse with which the instrument may be operated.

Activation of the jaws of conventional forceps-type instruments is limited to a single plane, i.e., the plane including the forceps jaws. Because the plane including the forceps jaws is generally coincident with the plane in which the handles move, the surgeon's hand frequently must be uncomfortably rotated to a position which accommodates the necessary displacements of the handles. In order to properly position the instrument, it is necessary to rotate the entire hand at the surgeon's elbow or at the shoulder. Such movements are quite crude in comparison to movements created by the intrinsic hand muscles and limit the degree of precision with which the jaws may be controlled.

Another problem with conventional forceps-type instruments is that the desired force to be applied by the jaws to an object must be manually maintained. This may further add to the discomfort during use as the surgeon squeezes the handle and simultaneously rotates the hand. Inevitably, the force exerted by the jaws varies as the hand is repositioned. This may result in the needle or other object held by the jaw slipping within the jaws or altogether falling out.

The prior art instruments are either in normally closed or open positions. For those in a normally closed position, a substantial amount of force must be exerted by the user to effect opening of the jaws. Since it is common to repeatedly open and close the jaws to effect a desired grip, as during a suturing operation, it is not uncommon for the user of such instruments to suffer hand fatigue. Those instruments that are normally open require a substantial amount of closing force which similarly fatigues the user's hand upon repeated manipulation of the jaws.

A still further problem with the prior art instruments is that the amount of pressure exerted by the jaws on an object cannot be readily consistently applied. Instead, the user roughly gauges the jaw pressure by the amount of pressure applied through the handles.

SUMMARY OF THE INVENTION

The present invention is directed to a surgical instrument having first and second cooperating jaws that are movable relative to each other selectively between open and closed positions, and structure for normally urging the jaws from their open position towards their closed position with a first predetermined force, with there further being structure for urging the jaws towards the closed position therefor with a second predetermined force that is greater than the first predetermined force.

With the inventive structure, a first predetermined force can be applied to initially seat an object between the jaws. Once the object is situated as desired, the second predetermined force can be applied to the jaws to firmly hold the object in place.

With the inventive structure, the user does not have to work against a large force to grip and regrip the object with the first predetermined force. This minimizes hand and arm fatigue. The second predetermined force is preferably sufficient to positively hold the object between the jaws.

In one form, the instrument has an elongate body and a sleeve that is slidable relative to the body and against at least one of the first and second jaws to urge the jaws towards the closed position therefor.

In one form, the structure for applying the first predetermined force is a coil spring that biases the sleeve against the one of the first and second jaws to produce the first predetermined force.

The structure for applying the second predetermined closing force may take a variety of different forms. In one form, a luer lock is used to force the sleeve against the jaws. In another form, the second structure is made up of first and second links pivoted to each other and movable to an overcenter position in which the first and second links act between the body and the sleeve. The invention contemplates use of one or more of such link pairs.

In one form, there is a slider on the body and a guide block on the body that is movable lengthwise relative to the body. A spring acts between the guide block and the sleeve and the second structure acts between the slider and the guide block.

The invention also contemplates the provision of a ratchet structure to maintain the second predetermined closing force on the jaws. As a result, the user does not have to manually maintain a constant force on the jaws. The result is the reduction in hand and arm fatigue and the application of a constant closing force on the jaws.

To further prevent arm fatigue and facilitate manipulation, particularly in tight spaces, the instrument, in one form, has an overall cylindrical configuration. In one form, there is rounded end cap to be placed in the palm of a user's hand. A cylindrical finger grip can be grasped by adjacent fingers on the same hand in which the end cap is placed and drawn by the adjacent fingers towards the end cap to move the jaws towards the open position therefor.

In one form, the instrument has an elongate body and an operating rod that connects to at least one of the jaws. There is cooperating structure on the operating rod and jaws for moving the jaws towards an open position as the rod moves in a first direction relative to the body, and moving the jaws towards a closed position as the rod moves in a second direction opposite to the first direction relative to the body.

In one form, the first structure includes a first spring for urging the rod in the first direction and a second spring for urging the rod in the second direction. The rod, in an equilibrium position therefor, urges the jaws towards the closed position with the first predetermined force.

In one form, the second structure urges the rod in the second direction from the equilibrium position therefor against the force exerted by the first spring in the first direction.

The invention also contemplates a surgical instrument having an elongate body, first and second cooperating jaws movable relative to each other selectively between open and closed positions therefor, an operating rod, structure for connecting the operating rod to the body for movement relative to the body to selectively place the jaws in the open and closed positions therefor, first and second grips for selectively moving the operating rod relative to the elongate body, and cooperating structure on the first and second grips, elongate body and operating rod for causing the first grip to move in a first direction relative to the body without the second grip moving relative to the body as an incident of the first and second grips being squeezed towards each other until a first predetermined force is applied to at least one of the jaws to urge the jaws towards the closed position with the first predetermined force, whereupon additional squeezing of the grips causes the second grip to move in a second direction opposite to the first direction relative to the body without the first grip moving relative to the body to develop a second predetermined force on at least one of the jaws to urge the jaws towards the closed position.

In one form, the first and second grips project transversely to the length of the elongate body to thereby define a pistol-type arrangement for the first and second grips.

In one form, there is a ratchet structure for releasably maintaining the second predetermined force on the jaws without the user's having to squeeze the grips towards each other. A movable trigger can be provided for selectively releasing the ratchet structure.

In one form, the grips are normally biased away from each other.

In one form of the invention, the operating rod is fixedly connected to the first grip.

In another form of the invention, the body is cylindrical and there is a sleeve that is connected with the body and the operating rod, with the sleeve residing radially between the body and the operating rod and fixedly connected to the second grip.

In one form, the second predetermined force is applied by the sleeve acting against at least one of the jaws.

The invention also contemplates an instrument having first and second cooperating jaws movable relative to each other selectively between open and closed positions, structure for normally urging the jaws from the closed position toward the open position therefor, first structure for urging the jaws into the closed position therefor with a first predetermined force, and second structure for urging the jaws into the closed position therefor with a second predetermined force that is greater than the first predetermined force.

In one form, the second structure is separate from the first structure.

The invention also contemplates the provision of structure for releasably maintaining a predetermined closing force on the jaws only upon operation of the second structure.

DETAILED DESCRIPTION OF THE DRAWINGS

Figure 1:
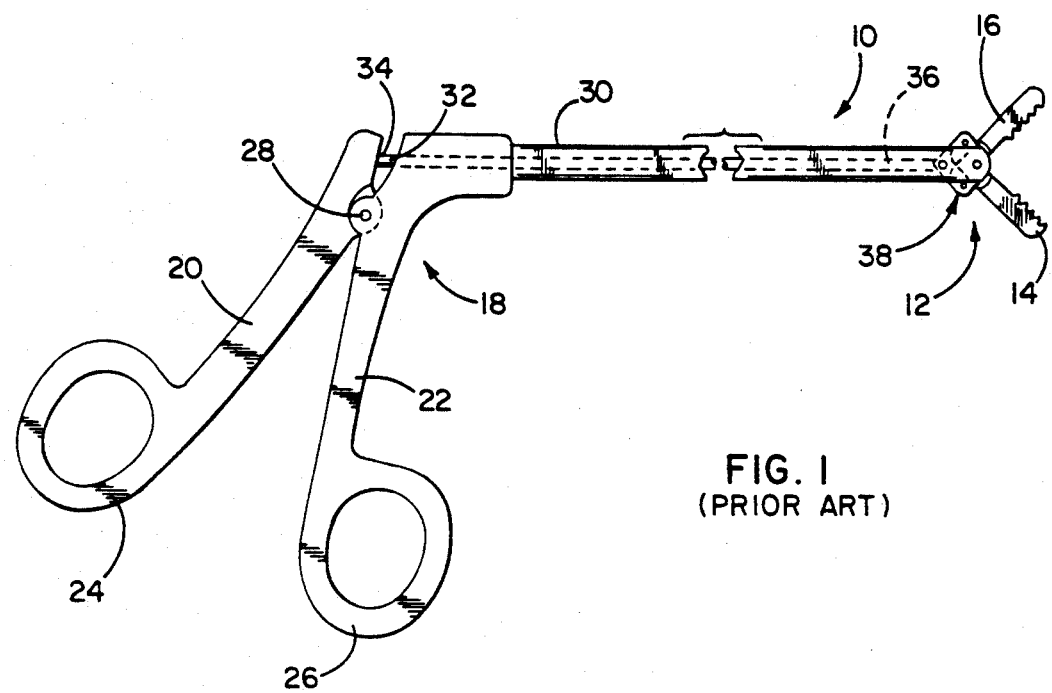
FIG. 1 is a side elevation view of a conventional forceps-type gripping instrument.

In FIG. 1, a conventional forceps-type instrument is shown at 10. The instrument 10 has a working end 12 consisting of cooperating toothed jaws 14, 16, which are movable selectively towards and away from each other by operation of a remote handle 18, through which the instrument 10 is held and operated.

The handle 18 consists of two parts 20, 22, having grips/rings 24, 26, respectively, for reception of the fingers of the operator. The handle parts 20, 22 are pivotably joined by a pin 28 so that the handle parts 20, 22 operate in the same fashion as a conventional scissors.

The one handle part 22 carries a cylindrical sleeve 30 through which an operating rod 32 passes. The proximal end 34 of the rod 32 is connected to the handle part 20, with the distal end 36 of the rod 32 connected to an operating linkage 38 associated with the jaw pair 14, 16.

In the FIG. 1 position for the instrument 10, the jaws 14, 16 are in their open state. By squeezing the handle parts 20, 22 towards each other, the operating rod 32 is drawn from right to left relative to the sleeve 30, which moves the jaws 14, 16, from their open state in FIG. 1 to a closed state.

The force exerted by the jaws 14, 16 on an object therebetween is determined by the amount of pressure applied in squeezing the handle parts 20, 22. If the handle parts 20, 22 are released, the pressure exerted by the jaws 14, 16 is relaxed.

It can be seen that operation of the instrument 10 in FIG. 1 is somewhat awkward in that the user is required to squeeze the handle parts 20, 22 and may be required to rotate the entire instrument 10 to align the jaws 14, 16 in the desired orientation. This is because the jaws 14, 16 have a fixed orientation relative to the sleeve 30 and thus the handle parts 20, 22.

Figure 2:
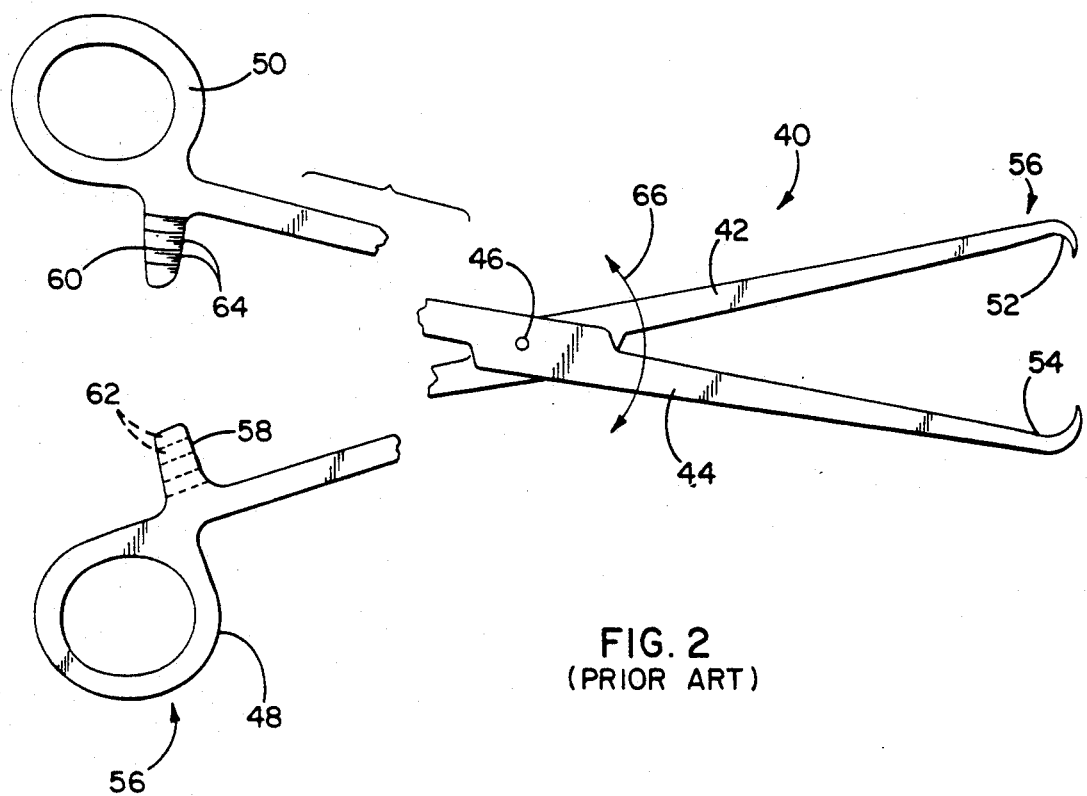
FIG. 2 is a side elevation view of another conventional forceps-type gripping instrument.

Part of the problem with operating the instrument 10 in FIG. 1 is overcome by another conventional instrument 40, shown in FIG. 2. The instrument 40 consists of elongate, crossing arms 42, 44 pivotably connected at their midportion by a pin 46 to have the overall general configuration of a scissors.

At the proximal end of the instrument 40, finger grips/rings 48, 50 are provided on the arms 42, 44, respectively. Offset gripping jaws 52, 54 are provided at the distal end 56 of the instrument 40.

By engaging and squeezing the finger grips/rings 48, 50 towards each other, at the proximal end 56 of the instrument 40, the jaws 52, 54 are urged towards each other. Locking tabs 58, 60 are provided on the arms 42, 44 and each have stepped ramp surfaces 62, 64, respectively, which act against each other to produce a ratchet effect to thereby releasably lock the arms 42, 44 with different degrees of gripping pressure applied between the jaws 54, 56. By urging the engaged tabs 58, 60 away from each other in the line of the axis of the pin 46, the ramp surfaces 62, 64 can be released to open the instrument 40 to the state shown in FIG. 2.

In certain applications, it is inconvenient and awkward to squeeze the grips 48, 50 towards each other and to at the same time rotate the instrument 40 about its length, as indicated by double-headed arrow 66. An additional problem with the instrument 40 in FIG. 2 is that the ratchet mechanism defined by the tabs 58, 60 engages as the jaws 52, 54 approach a gripping position. If it is desired to release and re-grip an object, the ramp surfaces 62, 64 must be disengaged by pressing and rotating the arms 42, 44 clockwise or counterclockwise against one another. This required manual force may cause hand fatigue and/or tremors with repetition procedures. Also, during re-gripping, an object held by the maws 52, 54 may be inadvertently released.

Another problem with each of the prior art apparatus 10, 40 in FIGS. 1 and 2, respectively, is that both are normally held by the user so that rotation of the device about its length requires that the user pivot his/her arm at the shoulder. This is a very burdensome maneuver, particularly where very precise and delicate maneuvers are required during surgical procedures.

Figure 3:
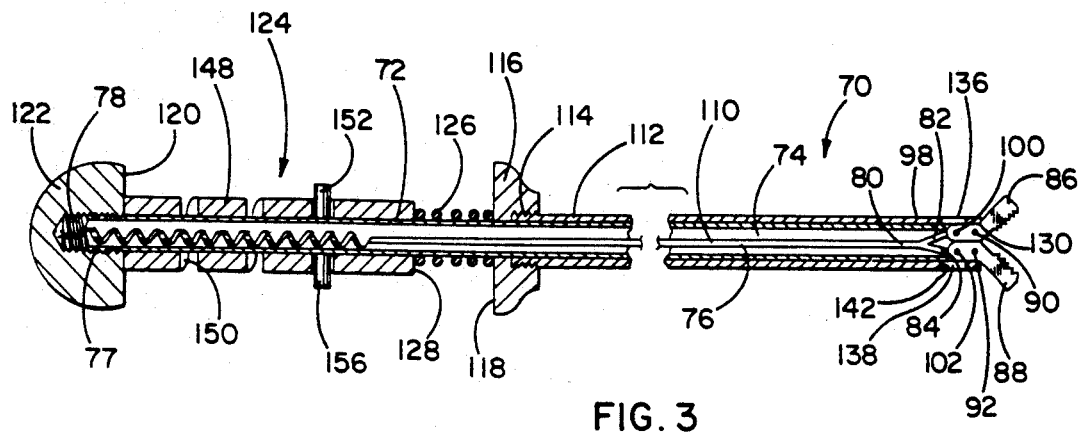
FIG. 3 is a sectional view of an instrument according to the present invention with a pair of gripping jaws thereon in an open position.
Figure 4:
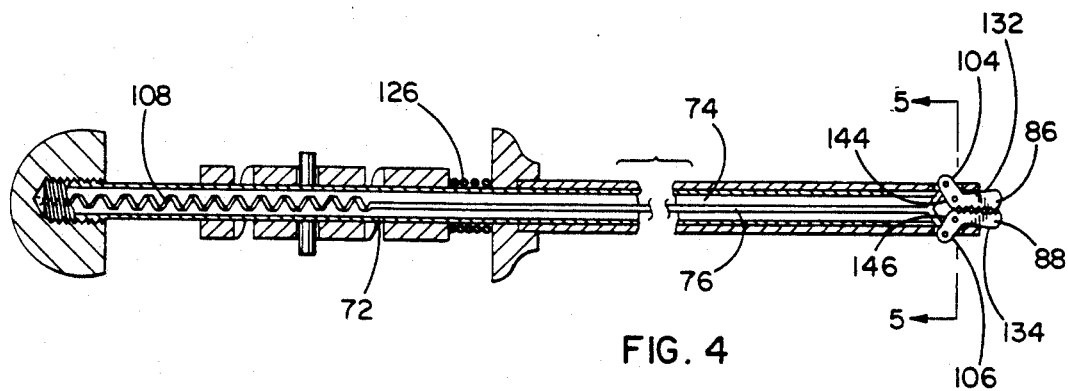
FIG. 4 is a view as in FIG. 3 with the jaws in a closed position.
Figure 5:
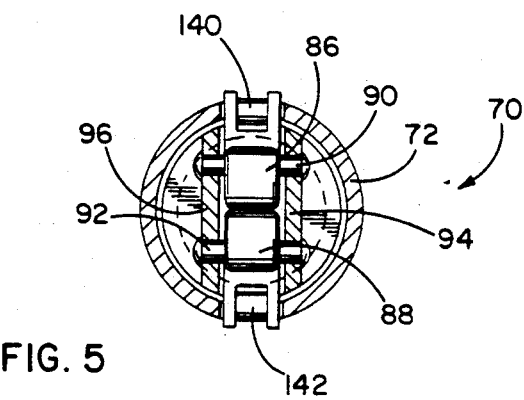
FIG. 5 is a cross-sectional view of the jaws taken along line 5—5 of FIG. 4.

In FIGS. 3-5, a first embodiment of the inventive instrument is shown at 70. The instrument 70 has an elongate, cylindrical body 72 with a through opening 74 receiving an operating rod 76. The operating rod 76 has a proximal end 77 embedded in a thickened end 78 of the body 72. The distal end 80 of the rod 76 is bifurcated to define legs 82, 84 which connect to first and second jaws 86, 88, respectively, which jaws 86, 88 are movable selectively between the normally closed position of FIG. 4 and the open position of FIG. 3.

The jaws 86, 88 are each generally L-shaped and are mounted for pivoting movement relative to the body 72 by pins 90, 92. The pins 90, 92 captively hold the jaws 86, 88 between flanking wall parts 94, 96, that may be defined by flattening the body 72 at its distal end 98 or, alternatively, the walls 94, 96 can be fitted within the cylindrical distal end 98 of the body 72. The legs 82, 84 of the rod 76 are pivotably connected by pins 100, 102 to operating arms 104, 106 on the jaws 86, 88, respectively.

The legs 82, 84 are, in a normal state, spread away from each other as in FIG. 4 so as to tend to normally urge the jaws 86, 88 toward the closed position of FIG. 4. The proximal end 108 of the rod 76 is coiled to act as a compression element between the end 78 and the undeformed length 110 of the rod 76, to thereby normally exert a left-to-right bias on the undeformed length 110 of the rod 76 to thereby weakly urge the jaws 86, 88 towards a closed state, thereby providing a weak countertension on the application. The purpose of the coiled part of the rod 76 is to absorb possible abnormal stress on the jaws 86, 88 secondary to excessive closure force due to a fixed clamping of thick tissues, or other objects.

An operating sleeve 112 surrounds the body 72 so as to be guided thereover from left to right in FIGS. 3 and 4. The sleeve 112 has a threaded end 114 to releasably engage a finger grip 116. The finger grip 116 defines an axially facing surface 118 which, with an axially oppositely facing surface 120 on an end cap 122, threaded to the body 72, captively maintains a luer lock assembly 124 and a coil spring 126 in an operative position on the instrument 70. The luer lock assembly 124 is selectively movable between a release position, shown in FIG. 3, and a clamped position shown in FIG. 4.

With the luer lock assembly 124 in its release position of FIG. 3, the coil spring 126 acts between an axially facing end surface 128 on the lock assembly 124 and the grip surface 118 to bias the finger grip 116, and thereby the operating sleeve 112, towards the right in FIGS. 3 and 4, which bears an interior, annular corner 130 of the body 72 against the jaws 86, 88 to thereby squeeze the jaws 86, 88 into the closed position therefor. The jaws 86, 88 have cam surfaces 132, 134, respectively, which diverge from left to right so that there is a progressively increasing wedging force exerted by the corner 132 of the body 72 on the jaws 86, 88 as the body 72 is directed form left to right in FIGS. 3 and 4. Cut-outs 136, 138 are provided through the body 72 at diametrically opposite locations to accommodate the operating arms 104, 106, which project through the body 72 upon the jaws 86, 88 realizing their closed position.

The spring 126 is shown partially compressed in FIG. 3. Upon the spring 126 extending fully, the sleeve 112 effects closing of the jaws 86, 88. With the luer lock assembly 124 in the release position of FIG. 3 and the spring 126 fully extended, body edges 140, 142 are placed in abutting relationship to rearwardly facing edges 144, 146 on the operating arms 104, 106 so that a first predetermined force is applied to the jaws 86, 88.

The luer lock assembly 124 has a slider 148 with a spiral groove 150 formed therein to cooperate with diametrically oppositely projecting guide pins 152, 156, carried by the body 72. The pins 152, 156 are preferably removable to facilitate disassembly of the instrument 70 as for purposes of cleaning and/or repair. Rotation of the slider 148 in one direction advances the slider 148 from the release position of FIG. 3 towards the right into the FIG. 4 position. As this occurs, the slider surface 128 compresses the spring 126 against the grip surface 118 and thereby exerts on the sleeve 112 a force that exceeds the predetermined force exerted on the sleeve 112 by the spring 126. The second predetermined force enhances the first predetermined force by increasing the squeezing force by the annular corner 130 of the body 72 on the jaws 86, 88 and additionally by bearing the edges 140, 142 against the jaw arms 104, 106. Further, since the slider 148 on the luer lock assembly 124 becomes fixed, the instrument 70 becomes releasably locked thereby.

It can be seen that the instrument 70 can be conveniently held in the palm of a user's hand. Rotation of the instrument can be effected by the user's turning of his/her wrist without requiring a repositioning of the entire arm at either the elbow or the shoulder. Additionally, the device is readily disassembled to facilitate its cleaning and/or repair. By removing the end cap 122 and releasing the guide pins 152, 156 from the body 72, the luer lock assembly 124 and coil spring 126 are slidable from right to left over the body 72 and, in turn, the body 72, with the attached rod 76 and jaws 86, 88 is slidable from left to right out the free distal end 98 of the sleeve 112.

A further embodiment of the invention is shown at 160 in FIGS. 6-9. The instrument 160 functions very similarly to the instrument 70 in FIGS. 3-5, with the primary distinctions residing in the assembly at 162 for exerting a supplemental gripping force on a pair of cooperating jaws 164, and a modification to the mechanism of the jaw pair 164.

More particularly, the assembly 162 consists of a slider 166, which abuts to an end cap 168. The slider 166 is connected through a linkage 170 to a guide block 172, which is movable lengthwise relative to a body 173, corresponding to the body 72 on the instrument 70.

Figure 6:
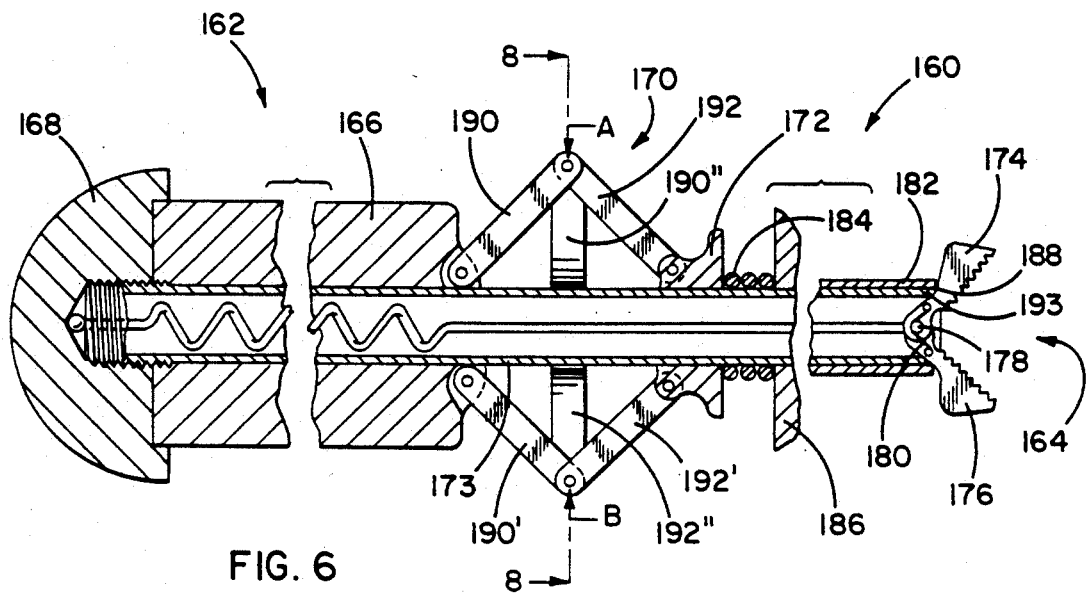
FIG. 6 is a sectional view of a modified form of instrument according to the present invention and utilizing an overcenter linkage to squeeze the jaws on the instrument to a closed position, with the jaws shown in an open position and the overcenter linkage in a release position.
Figure 7:
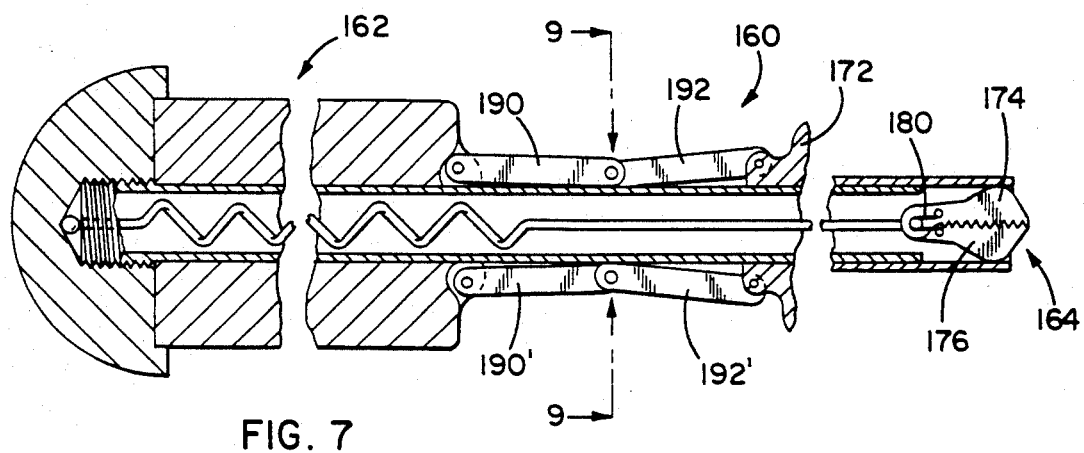
FIG. 7 is a view as in FIG. 6 with the overcenter linkage in a clamped position and the jaws in a closed position.

The jaw pair 164 consists of first and second jaws 174, 176 connected by a pin 178 for pivoting movement between an open position, shown in FIG. 6, and a closed position, shown in FIG. 7. A torsion spring 180 normally maintains the jaws 174, 176 in an open state. The jaw pair 164, however, remains in a normally closed state. An operating sleeve 182 is biased by a coil spring 184, which acts between the guide block 172 and a finger grip 186, to thereby urge the finger grip 186 and sleeve 182, on which the grip 186 is attached, to the right in FIGS. 6 and 7, to thereby bear an annular corner 188 on the sleeve 182 against both jaws 174, 176 to progressively squeeze the jaws 174, 176 towards the closed position of FIG. 7.

Figure 8:
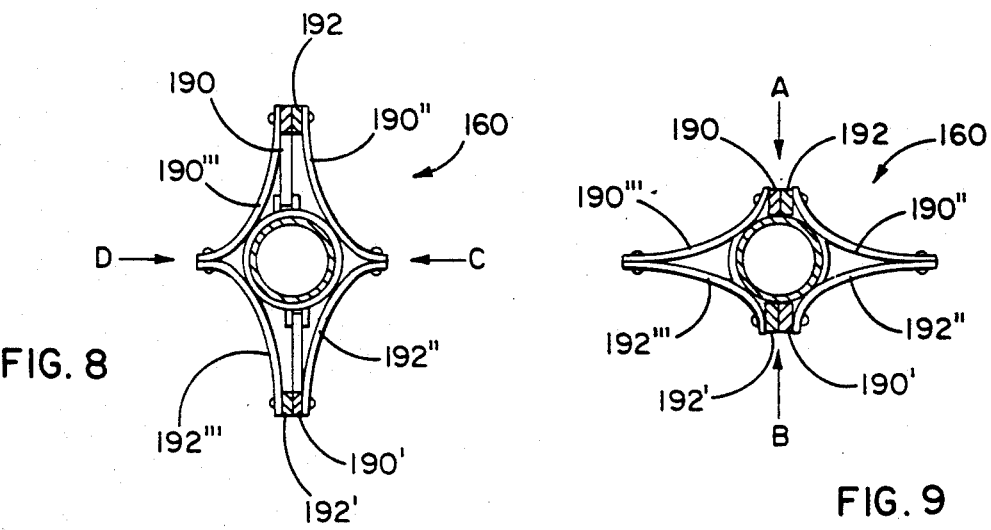
FIG. 8 is a cross-sectional view of the overcenter linkage taken along line 8—8 of FIG. 6.
Figure 9:
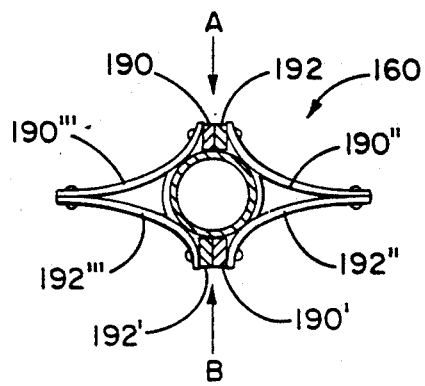
FIG. 9 is a cross-sectional view of the overcenter linkage taken along line 9—9 of FIG. 7.

The linkage 170 is provided to exert a supplementary closing force on the jaws 174, 176 that exceeds the first force provided by the sleeve 182 through the spring 184. The linkage consists of four overcenter link pairs 190, 192; 190', 192'; 190'', 192''; 190''', 192'''. With the instrument 160 in the FIG. 6 orientation, the user can press down on the link pairs 190, 192 and 190', 192' at diametrically opposite locations, as indicated by the arrows A and B, which collapses the link pairs 190, 192 and 190', 192' to the overcenter position shown in FIG. 7. This results in the effective extension of the combined length of the links 190, 192 and 190', 192'. At the same time, this expands the link pairs 190'', 192''; 190''', 192''' radially outwardly from the FIG. 8 position to that shown in FIG. 9, corresponding to the FIG. 6 position for the link pairs 190, 192, 190', 192'. To draw the links 190, 192; 190', 192' out of their overcenter orientation in FIG. 7, the link pairs 190'', 192''; 190''', 192''' are reoriented by pressing at diametrically opposite locations thereon, as indicated by the arrows C and D in FIG. 8. This collapses the links 190, 192; 190', 192' and causes the links 190'', 192''; 190''', 192''' to be placed into overcenter relationship, corresponding to the relationship for the links 190, 192; 190', 192' in FIG. 7. The lengths of the various links 190, 192; 190', 192'; 190'', 192''; 190''', 192''' are chosen so that the spacing between the slider 166 and guide block 172 is maximized with the links 190, 192; 190', 192'; 190'', 192''; and 190''', 192''' in the orientation shown in FIGS. 7 and 9, whereas the same distance is minimized with the links 190, 192; 190', 192'; 190'', 192''; and 190''', 192''' positioned as shown in FIGS. 6 and 8.

The distal edge 193 of the body 173 abuts the jaws 174, 176 to limit the amount of opening, as shown in FIG. 6, with the sleeve 182 withdrawn. With the sleeve 182 withdrawn and the jaws 174, 176 open as in FIG. 6, the user can place the object to be picked up in the mouth of the jaws 174, 176. By releasing the grip 186, the spring 184 drives the sleeve 182 from left to right over the jaws 174, 176 to close the jaws 174, 176 with a predetermined force. If the object is not positioned as desired between the jaws 174, 176, the user can retract the sleeve 182 and effect regripping. Once the desired grip is obtained, the user can then press on the link pairs 190, 192, 190', 192' to thereby squeeze the jaws 174, 176 with an additional gripping force to thereby positively maintain an object held by the jaws 174, 176.

The instrument 70 is operable in generally the same fashion as the instrument 160. Both instruments 70, 160 can be conveniently held with the end caps 122, 168 comfortably fitting in the palm of the user's hand, in which position the finger grips 116, 186 are readily grasped between the index and adjacent fingers and drawn towards the palm to retract the sleeves 112, 182. The instrument 160, as the instrument 70, can be conveniently rolled and rotated by the user with intrinsic muscles of the hand and/or rotated through the process of supination/pronation effected by the elbow joint.

Figure 10:
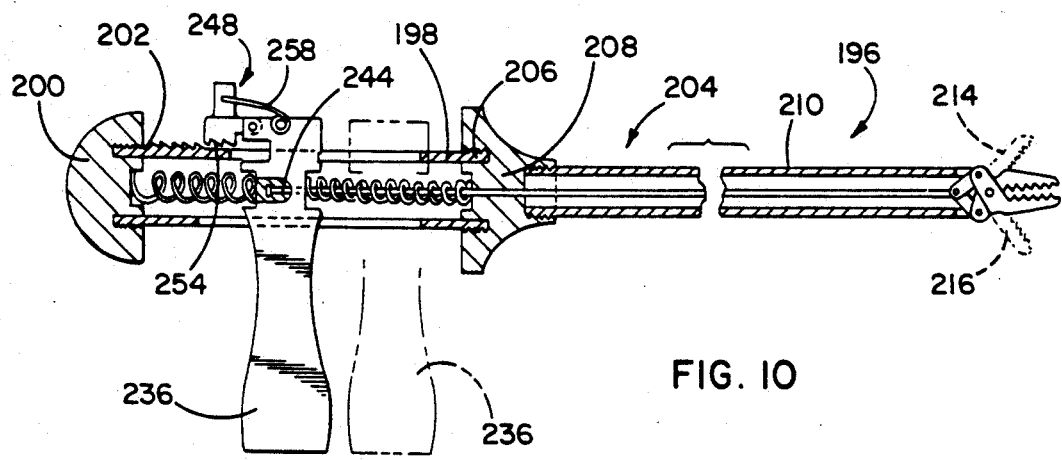
FIG. 10 is a cross-sectional view of a further modified form of instrument according to the present invention and showing the jaws thereon in a closed state with a closing force exerted on the jaws that is less than the maximum closing force.
Figure 11:
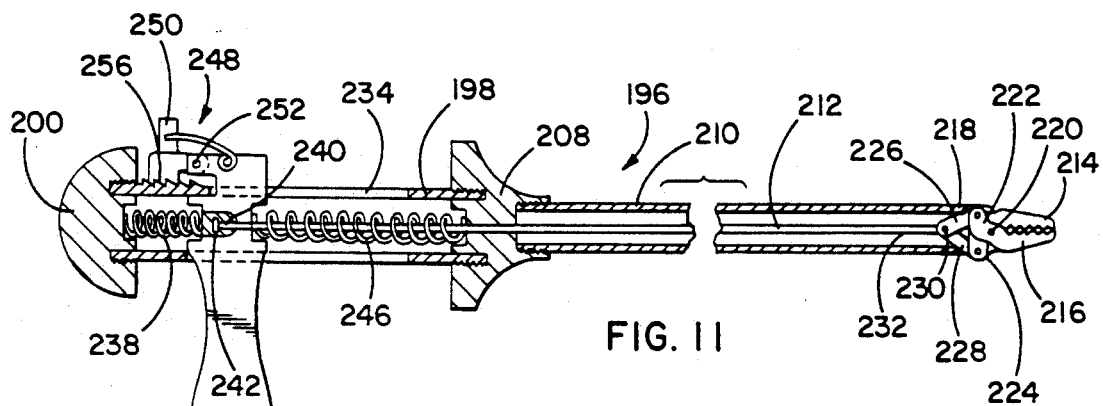
FIG. 11 is a view as in FIG. 10 with a greater clamping force being applied to the jaws than is being applied with the instrument positioned as in FIG. 10.

A further embodiment of the invention is shown in FIGS. 10 and 11 at 196. The instrument 196 has a main body 198 with a removable end cap 200, threaded to its proximal end 202, and a sleeve assembly at 204 threaded onto its distal end 206. The sleeve assembly 204 consists of a finger grip 208, threaded directly onto the body 198, and a sleeve 210 threaded in turn onto the finger grip 208.

An elongate operating rod 212 extends partially through the length of the body 198 and into the sleeve 210 for engagement with a pair of jaws 214, 216 at the distal end 218 of the sleeve 210. The jaws 214, 216 are pivotable about a pin 220 supported on, and linked to, the sleeve 210 at diametrically opposite locations thereon. The jaws 214, 216 have offset arms 222, 224 which are engaged, respectively, with driving links 226, 228, pivotably connected by a pin 230 to the distal end 232 of the operating rod 212.

By advancing the rod 212 from left to right in FIGS. 10 and 11, the links 226, 228 are caused to drive the jaws 214, 216 in rotation oppositely about the pivot pin 220. This effects opening of the jaws 214, 216 to the position shown therefor in phantom. By drawing the rod 212 towards the left in FIGS. 10 and 11, the jaws 214, 216 are caused to pivot to close the jaws 214, 216, as shown in solid lines in FIG. 10.

The body 198 has a slot 234 in which a hand grip 236 is received for guided movement lengthwise of the instrument 196. A first coil spring 238 acts between the end cap 200 and the hand grip 236 to urge the hand grip 236 from left to right in FIGS. 10 and 11. The proximal end 240 of the rod 212 has an enlarged head 242 thereon which nests in a conforming seat 244 in the hand grip 236. Through this arrangement, the rod 212 follows lengthwise movement of the grip 236. Resultingly, the spring 238 urges the grip 236 and the rod 212 carried thereby towards the open position. A second coil spring 246 acts between the hand grip 236 and finger grip 208 so as to urge the hand grip 236 and rod 212 in a right-to-left direction in FIGS. 10 and 11.

The spring constants for the springs 238, 246 are chosen such that the hand grip 236 realizes an equilibrium position in which a first predetermined closing force is exerted on the jaws 214, 216. To accomplish this, the compressive closing force of the spring 246 overcomes the compressive opening force of the spring 238. According to the invention, a supplemental closing force can be applied and maintained by a ratchet assembly 248. The ratchet assembly 248 consists of a toothed locking plate 250, connected for pivoting movement relative to the upper portion of the handle 236 by a pin 252. The locking plate 250 has a plurality of teeth 254 which cam over and lock to complementary teeth 256 on the proximal end 202 of the body 198. A torsion spring 258 maintains a constant counterclockwise bias on the locking plate 250 in FIGS. 10 and 11.

With the described structure, the jaws 214, 216 are in a normally closed state. The user grabs the finger grip 208 between the index finger and adjacent finger and with the thumb or palm can draw the hand grip 236 towards the finger grip 208, which causes the jaws 214, 216 to open. Once the object is placed between the jaws 214, 216, the grip 236 can be released, which results in the jaws 214, 216 closing with a force determined by the difference between the forces exerted by the springs 238, 246. When it is desired to place an additional gripping force on the jaws 214, 216, and to effect locking thereof, the user places the end cap 200 in the palm of the hand and draws the grip 236 back towards the palm to cause the teeth 254 on the locking plate 250 to ride over the teeth 256, to thereby releasably fix the hand grip 236 in a plurality of different positions relative to the end cap 200. This results in a greater force being applied to the jaws 214, 216 than the first predetermined force resulting solely from the action of the spring 246. Under such circumstances, the spring 246 will be elongated beyond its resting, undeformed state under the influence of the stronger manual force.

To effect release of the locking plate 250, the user draws the grip 236 towards the end cap 200 slightly and then pivots the plate 250, as with his/her thumb, to disengage the teeth 254, 266, which then results in the spring 246 overcoming the force of the spring 238 to drive the hand grip 236 back to its equilibrium position in which the jaws 214, 216 are closed with the aforementioned first predetermined force.

Figure 12:
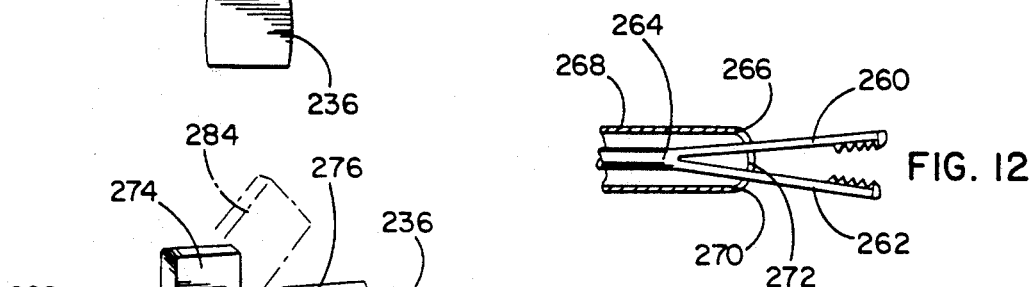
FIG. 12 is a fragmentary side elevation view of a modified form of jaw shown in an open state.
Figure 12:

FIG. 12 shows a modified form of jaw arrangement useable with the previously described structures. In FIG. 12, jaws 260, 262 are integrally formed with an operating rod 264 and are normally biased away from each other to an open position shown in FIG. 12. The jaws 260, 262 normally project out of the open free end 266 of a sleeve 268 at the working end of the instrument. By retracting the rod 264, by movement thereof from right to left in FIG. 12, the jaws 260, 262 are compressed towards each other and thereby closed upon encountering the annular shoulder 270 bounding the opening 272, through which the jaws 260, 262 project.

Figure 13:
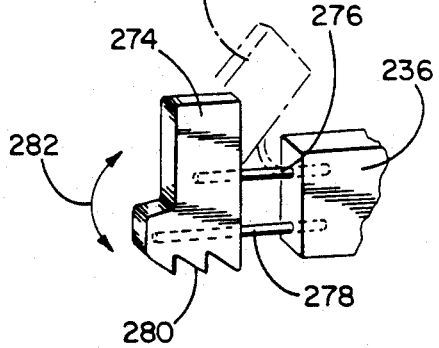
FIG. 13 is a perspective view of a ratchet mechanism useable on the instrument in FIGS. 10 and 11 to maintain a closing force on the jaws.
Figure 14:
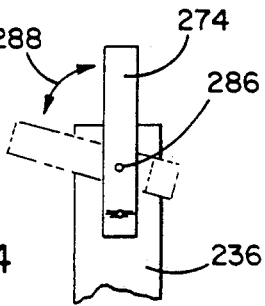
FIG. 14 is a fragmentary plan view of a modified form of ratchet assembly.
Figure 15:
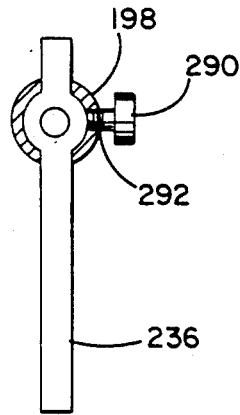
FIG. 15 is an end view of a locking mechanism for releasably maintaining the jaws in a desired relationship.

FIGS. 13 and 14 show a modified form of locking plate 274, corresponding to that 250 shown in FIGS. 10 and 11. In FIG. 13, the locking plate 274 is connected to the hand grip 236. Flexible, elongate rods 276, 278 are embedded in each of the hand grips 236 and plate 274 in substantially parallel relationship. The rods 276, 278 hold the locking plate 274 in a downward position, in which the teeth 280 thereon engage the teeth 256 on the body 198. At the same time, the rods 276, 278 permit a modicum of flexing of the plate 274 in an arcuate path, indicated by the double-headed arrow 282. This flexing allows a ratchet connection to be effected and also permits the locking plate 274 to be released by drawing it in a clockwise direction from the solid line position of FIG. 13 to the phantom position 284.

FIG. 14 shows an alternative arrangement for the locking plate 274. More particularly, a pivot pin 286 allows the plate 274 to rotate relative to the hand grip 236 about a vertical axis to move the teeth 280 in an arc as indicated by double-headed arrow 288. The user can thus readily disengage the locking plate 274 by pivoting the locking plate 274 to either side relative to the hand grip 236.

Another feature contemplated by the invention is the provision of a set screw 290 which permits the hand grip 236 to be locked in a desired position relative to the body 198. The set screw 290 is threaded into a bore 292 through the body 198 and against the hand grip 236 to effect locking of the hand grip 236 relative to the body 198.

Figure 16:
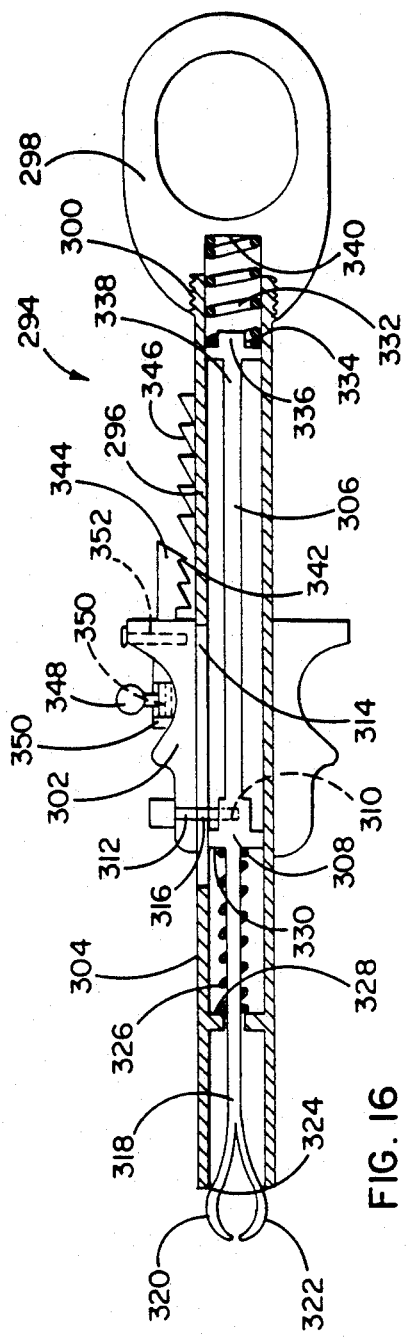
FIG. 16 is a cross-sectional view of a still further modified form of instrument according to the present invention.

A further alternative embodiment of the invention is shown at 294 in FIG. 16. The instrument 294 has an elongate, cylindrical body 296 having a thumb ring 298 threaded on the proximal end 300 of the body 296.

A finger grip 302 is slidable lengthwise guidingly along the outside surface 304 of the body 296. An operating rod 306 is movable lengthwise within the body 296. The rod 306 has an enlargement 308 on a midportion thereof. The enlargement has a blind bore 310 therein to threadably accept a guide pin 312, which projects through the finger grip 302, through a slot 314 in the body 296, and into the enlargement 308. The body 316 of the pin 312 is guided in the slot 314 in a lengthwise direction relative to the body 296.

At the distal end 318 of the rod 306, are integrally connected, cooperating jaws 320, 322. Movement of the rod 306, from left to right in FIG. 16, causes the annular corner 324 on the body 296 to squeeze the jaws 320, 322 against each other into a closed position.

A first coil spring 326 surrounds the rod 306 and acts between an annular shoulder 328, projecting radially inwardly from the body 296, and an oppositely facing shoulder 330 defined by the enlargement 308. The spring 326 exerts a first predetermined force on the rod 306, from left to right in FIG. 16, to close the jaws 320, 322 with a first predetermined force.

A second spring 332 acts between an axially facing shoulder 334, defined by a second enlargement 336 on the proximal end 338 of the rod 306, and the base surface 340 of a blind bore in the thumb ring 298. The spring 332 has a larger spring force than the spring 326. The spring 326, in normally biasing the rod 306, does not significantly compress the spring 332.

To enhance the first predetermined gripping force exerted by the spring 326 on the jaws 320, 322, the user draws the finger grip 302 towards the thumb ring 298 so that the guide pin 312 draws the rod 306, from left to right to FIG. 16, to thereby compress the spring 332. This occurs only after movement through the first range of closure, under the first predetermined for has been accomplished. As this occurs, teeth 342 on a ratchet bar 344 engage and progressively cam and lock with teeth 346 on the outside surface 304 of the body 296.

To release the ratchet bar 344 with the teeth 342, 346 engaged, a pivotable trigger 348 is provided. The trigger 348 is pivoted about a lengthwise pin 350 and engages a forwardly projecting portion 350 of the ratchet bar 344, and thereby pivots the ratchet bar 344 relative to a mounting pin 352, defining a vertical pivot axis for the ratchet bar 344.

With the described structure, the user can place the thumb in the thumb ring 298, and with the finger grip 302 between the index and adjacent fingers, slide the finger grip 302 forwardly against the bias of the spring 326. This exposes the jaws 320, 322 completely outside of the body 296. The jaws 320, 322, which are normally biased away from each other, thereby assume an open position. By releasing the finger grip 302, the spring 326 drives the rod 306 to the closed position of FIG. 16. Thereafter, the user can draw the finger grip 302 towards the thumb ring 298 to draw the rod 306 from left to right, to thereby further squeeze the jaws 320, 322 to enhance the clamping force exerted thereby on an object.

One particular advantage of the structure 194 in FIG. 16, which is also realized with the structures previously described, it that the user can readily open the jaws 320, 322 against a relatively weak spring force, to thereby open the jaws, 320, 322 and position an object to be picked up as desired. Regripping can be simply accomplished without fatigue on the hand of the user. once the object is in the desired grip position, the user can clamp the jaws 320, 322 with a firmer holding force. In the absence of this two-step arrangement, the user would be required to open the jaws 320, 322 against a more substantial force, which could result in hand fatigue after gripping and regripping of an object.

Figure 17:
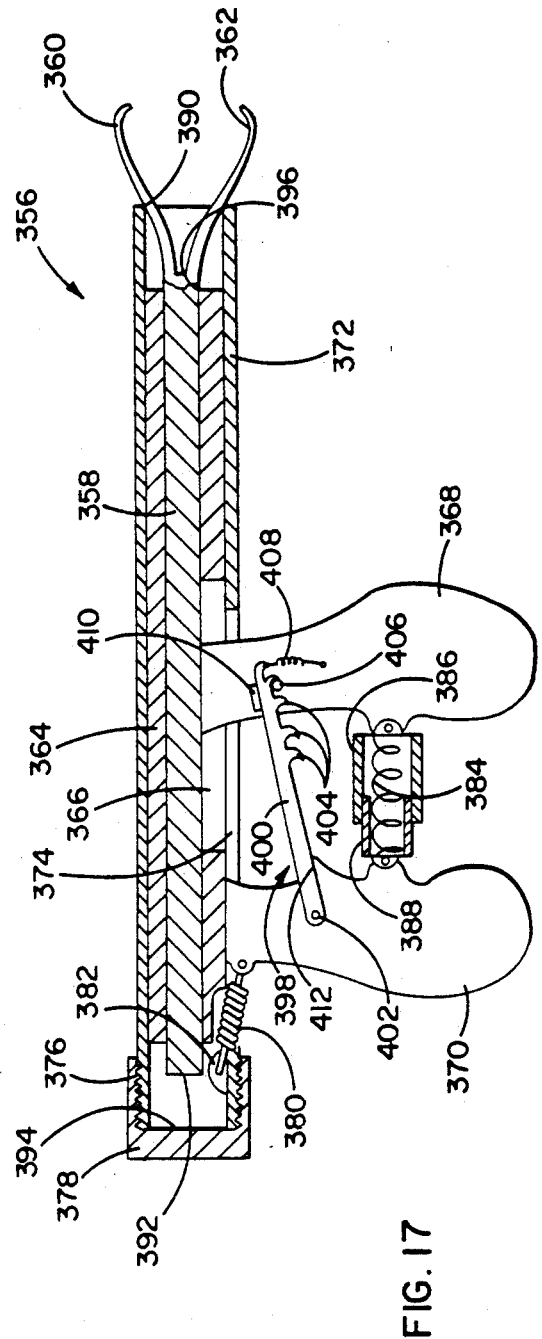
FIG. 17 is a cross-sectional view of a still further modified form of instrument according to the present invention.

A further embodiment of the invention is shown at 356 in FIG. 17. The instrument has an operating rod 358 with integrally formed jaws 360, 362, biased normally away from each other to an open state. The operating rod 358 is surrounded by a first sleeve 364, which has a slot 366 therethrough to accommodate a forward grip 368 that connects to the operating rod 358. A rear grip 370 connects to the first sleeve 364, so that by selectively squeezing the grips 368, 370 towards each other and moving them apart, the relative positions of the rod 358 and sleeve 364 can be changed.

A second sleeve 372 surrounds the first sleeve 364 and has a slot 374 to accommodate movement of the grips 368, 370. The proximal end 376 of the second sleeve 372 is threaded to releasably accept an end cap 378.

A stiff coil tension spring 380 connects between a tab 382 on the second sleeve 372 and the rear grip 370. The spring 380 resists forward movement (left to right in FIG. 17) of the rear grip 370.

A second, weaker coil compression spring 384 acts between the grips 368, 370, to urge the grips 368, 370 away from each other. A cup-shaped receptacle 386 is pivotably connected to the forward grip 368 and a similar cup-shaped receptacle 388 is pivotably connected to the rear grip 370. The receptacles 386, 388 are telescoped one within the other and define a confining envelope for the spring 384.

The spring 384, by urging the grips 368, 370 away from each other, biases the rod 358 towards the right in FIG. 17 to expose the jaws 360, 362 so that they spring to an open state. By squeezing the grips 368, 370, the forward grip 368 is moved rearwardly against the force of the spring 384 and towards the rear grip 370, which is prevented from moving forwardly by the stronger spring 380. Continued rearward movement of the forward grip 368 causes the annular edge 390 of the second sleeve 372 to squeeze the jaws 360, 362 together to a closed state with a first predetermined force. As the forward grip 368 continues to move rearwardly, the rear edge 392 of the rod 358 is brought into engagement with a blocking surface 394 on the end cap 378. At this point, rearward movement of the rod 358 is arrested. Further squeezing of the grips 368, 370, causes the rear grip 370 to move forwardly against the force of spring 380, thereby moving the first sleeve 364 from left to right. Eventually the annular corner 396 of the first sleeve 364 encounters the jaws 360, 362 and produces an enhanced squeezing force thereon to supplement the force exerted by the corner 390 of the second sleeve 372 on the jaws 360, 362.

A ratchet/lock is provided at 398 in the form of a bar 400 pivoted about a point 402 relative to the rear grip 370. The bar 400 has ratchet teeth 404 which engage a pin 406 on the forward grip 368. A spring 408 normally biases the bar 400 in a clockwise position in FIG. 17. This force is overcome as the handles 368, 370 are urged against each other so that the bar 400 repeatedly raises and drops to engage the pin 406 with the grips 368, 370 in different positions. An offset release tab 410 is provided on the bar 400 to raise the bar 400 and pivot the same in a counterclockwise direction to release the ratchet bar 400.

With this arrangement, the user can conveniently grip the object in the jaws 360, 362 by drawing the grips 368, 370 towards each other. A light closing pressure will be applied to the jaws 360, 362 before the rear handle 370 is required to move forwardly and the ratchet assembly 398 is actuated. An abutting surface 412 on the rear grip 370 abuts the ratchet bar 400 and limits the amount of clockwise pivoting to thereby situate the ratchet bar 400 in an operative position in which it is engageable with the pin 406 upon the grips 368, 370 being drawn towards each other.

The foregoing disclosure of specific embodiments is intended to be illustrative of the broad concepts comprehended by the invention.

I claim:

1. A surgical instrument comprising:
   a body;
   first and second cooperating jaws mounted on the body and movable relative to each other selectively between open and closed positions;
   first means on the body for normally urging said jaws from said open position toward said closed position with a first predetermined force and operable other than by relatively rotating any two threadably connected parts of said surgical instrument;
   means to be engaged by an operator to move the jaws from the closed position into the open position; and
   second means on the body for urging said jaws toward the closed position with a second predetermined force that is greater than said first predetermined force and operable other than by relatively rotating any two threadably connected parts of said surgical instrument.

2. The surgical instrument according to claim 1 wherein said body is elongate and the instrument includes a sleeve slidable relative to said body and against at least one of the first and second jaws to urge the jaws toward said closed position.

3. The surgical instrument according to claim 2 including means for opening the jaws against the first predetermined closing force, said opening means including a finger grip that is attached to said sleeve.

4. The surgical instrument according to claim 1 wherein there are ratchet means on at least one of the body and first and second means for releasably maintaining the second predetermined closing force on the jaws.

5. The surgical instrument according to claim 1 wherein said instrument has an overall cylindrical configuration.

6. The surgical instrument according to claim 1 wherein said instrument includes an elongate body and an operating rod that connects to at least one of the jaws, there being cooperating means on the operating rod and jaws for moving the jaws toward an open position as the rod moves in a first direction relative to the body and moving the jaws towards a closed position as the rod moves in a second direction opposite to the first direction relative to the body.

7. A surgical instrument comprising:
   an elongate body;
   first and second cooperating jaws on the elongate body movable relative to each other selectively between open and closed positions therefor;
   an operating rod;
   means for connecting the operating rod to the body for movement relative to the elongate body to selectively place the jaws in the open and closed positions therefor;
   means for selectively moving the operating rod relative to the elongate body,
   said moving means comprising first and second grips; and
   means, on the first and second grips, elongate body, and operating rod, for causing the first grip to move in a first direction relative to the body without said second grip moving relative to the body as an incident of the first and second grips being squeezed towards each other until a first predetermined force is applied to at least one of the jaws to urge the jaws toward said closed position with a first predetermined force, whereupon additional squeezing of said grips causes the second grip to move in a second direction opposite to said first direction relative to the body without said first grip moving relative to the body to develop a second predetermined force on at least one of the jaws to urge the jaws toward said closed position.

8. The surgical instrument according to claim 7 wherein the first and second grips project transversely to the length of the elongate body to thereby define a pistol-type arrangement for said first and second grips.

9. The surgical instrument according to claim 7 including ratchet means on at least one of the body, operating rod, moving means and cooperating means for releasably maintaining the second predetermined force on the jaws without a user's having to squeeze the grips towards each other.

10. The surgical instrument according to claim 9 including a movable trigger for selectively releasing the ratchet means.

11. The surgical instrument according to claim 7 including means for normally biasing the grips away from each other.

12. The surgical instrument according to claim 7 wherein the operating rod is fixedly connected to the first grip.

13. A surgical instrument comprising:
   a body;
   first and second cooperating jaws mounted on the body and movable relative to each other selectively between open and closed positions;
   first means on the body for normally urging said jaws from said open position toward said closed position with a first predetermined force;
   second means on the body for urging said jaws toward the closed position therefor with a second predetermined force that is greater than said first predetermined force,
   wherein said body is elongate and the instrument includes a sleeve slidable relative to said body and against at least one of the first and second jaws to urge the jaws toward said closed position,
   wherein said second means comprises first and second links pivoted to each other and movable to an overcenter position in which the first and second links exert a force between the body and the sleeve.

14. The surgical instrument according to claim 13 wherein there are third and fourth links acting between the body and the sleeve in the same manner as the first and second links.

15. A surgical instrument comprising:
   a body;
   first and second cooperating jaws mounted on the body and movable relative to each other selectively between open and closed positions therefor;
   first means on the body for normally urging said jaws from said open position toward said closed position therefor with a first predetermined force;
   second means on the body for urging said jaws toward the closed position therefor with a second predetermined force that is greater than said first predetermined force,
   wherein said instrument includes an elongate body and an operating rod that connects to at least one of the jaws, there being cooperating means on the operating rod and jaws for moving the jaws towards an open position as the rod moves in a first direction relative to the body and moving the jaws towards a closed position as the rod moves in a second direction opposite to the first direction relative to the body, wherein said first means includes a spring for urging the rod in the first direction and a second spring for urging the rod in the second direction, said rod in an equilibrium position urging the jaws towards the closed position therefor with said first predetermined force.

16. The surgical instrument according to claim 15 wherein said second means urges the rod in said second direction from the equilibrium position therefor against the force exerted by the first spring in said first direction.

17. A surgical instrument comprising:

a body;

first and second cooperating jaws on the body movable relative to each other selectively between open and closed positions;

means for normally urging said jaws from said closed position toward said open position;

first means on said body for urging said jaws into said closed position with a first predetermined force; and second means on said body for urging said jaws into the closed position with a second predetermined force that is greater than said first predetermined force, said first means being operable other than by relatively rotating any two threadably connected parts of said surgical instrument to produce said first predetermined force, said second means being operable other than be relatively rotating any two threadably connected parts of said surgical instrument to produce said second predetermined force.

18. The surgical instrument according to claim 17 including means for selectively maintaining a predetermined closing force on said jaws only upon operation of said second means.

19. A surgical instrument comprising:

a body;

first and second cooperating jaws mounted on the body and movable relative to each other selectively between open and closed positions therefor;

first means on the body for normally urging said jaws from said open position toward said closed position therefor with a first predetermined force;

second means on the body for urging said jaws toward the closed position therefor with a second predetermined force that is greater than said first predetermined force, wherein said body is elongate and the instrument includes a sleeve slidable relative to said body and against at least one of the first and second jaws to urge the jaws toward said closed position, wherein the first means comprises a coil spring on the body that biases the sleeve against the one of the first and second jaws to produce said first predetermined force.

20. A surgical instrument comprising:

a body;

first and second cooperating jaws mounted on the body and movable relative to each other selectively between open and closed positions;

first means on the body for normally urging said jaws from said open position toward said closed position with a first predetermined force;

second means on the body for urging said jaws toward the closed position therefor with a second predetermined force that is greater than said first predetermined force, wherein said body is elongate and the instrument includes a sleeve slidable relative to said body and against at least one of the first and second jaws to urge the jaws toward said closed position, wherein said second means comprises a luer lock to force the sleeve against the jaws to urge the jaws toward the closed position with said second predetermined force.

21. A surgical instrument comprising:

a body;

first and second cooperating jaws mounted on the body and movable relative to each other selectively between open and closed positions;

first means on the body for normally urging said jaws from said open position toward said closed position with a first predetermined force;

second means on the body for urging said jaws toward the closed position therefor with a second predetermined force that is greater than said first predetermined force, wherein said body is elongate and the instrument includes a sleeve slidable relative to said body and against at least one of the first and second jaws to urge the jaws toward said closed position, wherein there is a slider on the body and a guide block on the body both movable lengthwise relative to the body, a spring exerts a force between the guide block and the sleeve, and the second means exerts a force between the slider and the guide block.

22. A surgical instrument comprising:

a body;

first and second cooperating jaws mounted on the body and movable relative to each other selectively between open and closed positions;

first means on the body for normally urging said jaws from said open position toward said closed position therefor with a first predetermined force;

second means on the body for urging said jaws toward the closed position therefor with a second predetermined force that is greater than said first predetermined force, wherein said body is elongate and the instrument includes a sleeve slidable relative to said body and against at least one of the first and second jaws to urge the jaws toward said closed position, there further being means for opening the jaws against the first predetermined closing force, said opening means including a finger grip that is attached to said sleeve, wherein there is a rounded end cap on the body to be placed in the palm of a user and wherein with the end cap in a user's palm, the finger grip can be grasped by adjacent fingers on the same hand in which the end cap is placed and drawn by the adjacent fingers toward the end cap to move the jaws towards the open position therefor.

23. A surgical instrument comprising:

an elongate body;

first and second cooperating jaws mounted on the elongate body and movable relative to each other selectively between open and closed positions;

an operating rod;

means for connecting the operating rod to the body and to at least one of the jaws for movement relative to the elongate body to selectively place the jaws in the open and closed positions;

means for selectively moving the operating rod relative to the elongate body, said moving means comprising first and second grips; and cooperating means on the first and second grips, elongate body, and operating rod for causing the first grip to move in a first direction relative to the body without said second grip moving relative to the body as an incident of the first and second grips being squeezed towards each other until a first predetermined force is applied to at least one of the jaws to urge the jaws toward said closed position with a first predetermined force, whereupon additional squeezing of said grips causes the second grip to move in a second direction opposite to said first direction relative to the body without said first grip moving relative to the body to develop a second predetermined force on at least one of the jaws to urge the jaws toward said closed position, wherein the operating rod is fixedly connected to the first grip, wherein the body is cylindrical and there is a sleeve that is concentric with the body and the operating rod, said sleeve residing radially between the body and the operating rod and fixedly connected to the second grip.

24. A surgical instrument comprising:

first and second cooperating jaws movable relative to each other selectively between open and closed positions;

means for normally urging said jaws from said closed position toward said open position;

first means for urging said jaws into said closed position with a first predetermined force; and second means for urging said jaws into the closed position with a second predetermined force that is greater than said first predetermined force, wherein there are means for selectively maintaining a predetermined closing force on said jaws only upon operation of said second means.

* * * * *